(12) United States Patent
Hsueh et al.

(10) Patent No.: US 10,457,621 B2
(45) Date of Patent: Oct. 29, 2019

(54) PROCESS FOR PREPARING ARYL KETONE

(71) Applicant: ETERNAL MATERIALS CO., LTD., Kaohsiung (TW)

(72) Inventors: Sheng-Yao Hsueh, Kaohsiung (TW); Chih-An Chen, Kaohsiung (TW); You-Han Lin, Kaohsiung (TW); Hao-Tien Bai, Kaohsiung (TW)

(73) Assignee: ETERNAL MATERIALS CO., LTD., Kaohsiung (TW)

( * ) Notice: Subject to any disclaimer, the term of this patent is extended or adjusted under 35 U.S.C. 154(b) by 298 days.

(21) Appl. No.: 15/229,204

(22) Filed: Aug. 5, 2016

(65) Prior Publication Data
US 2017/0036981 A1 Feb. 9, 2017

Related U.S. Application Data

(60) Provisional application No. 62/201,624, filed on Aug. 6, 2015.

(51) Int. Cl.
*C07C 45/28* (2006.01)
*C07C 67/313* (2006.01)
*C07C 45/27* (2006.01)
*C07C 29/62* (2006.01)

(52) U.S. Cl.
CPC .............. *C07C 45/28* (2013.01); *C07C 29/62* (2013.01); *C07C 45/27* (2013.01); *C07C 67/313* (2013.01); *C07C 2601/14* (2017.05)

(58) Field of Classification Search
CPC ...................................................... C07C 45/28
See application file for complete search history.

(56) References Cited

U.S. PATENT DOCUMENTS 8,252,959 B2  8/2012  End et al.
8,575,394 B2  11/2013  End et al.

FOREIGN PATENT DOCUMENTS

| CN | 1281845 | A | 0/2001 |
|---|---|---|---|
| CN | 1113840 | C | 7/2003 |
| CN | 101928208 | A | 12/2010 |
| CN | 103980101 | * | 8/2014 |
| CN | 103980101 | A | 8/2014 |

OTHER PUBLICATIONS

CN 10 398 0101 machine translation (2014).*
First Office Action from Taiwan Intellectual Property Office.
English Translation of Office Action and Search Report of the IPO—TW 105125059.
Second Office Action from Taiwan Intellectual Property Office.
English Translation of second Search Report of the IPO—TW 105125059.
CN101928208 A_Machine_English_translation_of_Description.
CNI01928208 A_Machine_English_translation_of_Abstract.
CN103980101 A_Machine_English_translation_of_Claims.
CNI03980101 A_Machine_English_translation_of_Abstract.
CN1113840 C_Machine_English_translation_of_Description.
CNI113840 C_Machine_English_translation_of_Abstract.
In-Shi Hu, et al.; Synthesis of 2-Hydroxy-2-methyl-1-propiophenone; Chemical World; vol. 4; Apr. 25, 2001; The abstract; Experimental Sections 1.2.1 to 1.2.4.
The_Office_Action_and_Search_Report dated Jun. 26, 2018.

(Continued)

*Primary Examiner* — Kuo Liang Peng
(74) *Attorney, Agent, or Firm* — Ladas & Parry LLP

(57) ABSTRACT

A process for preparing aryl ketones is disclosed. The process includes photo-oxidizing a compound of formula (V), (VI), (VII) or (VIII):

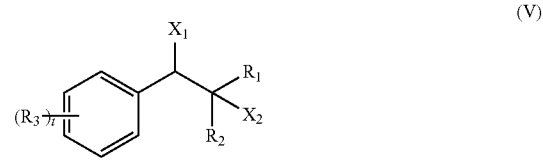

(V)

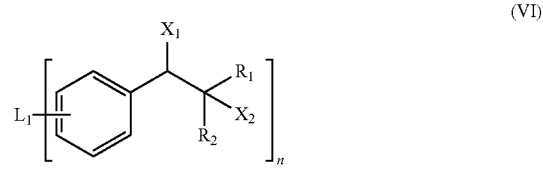

(VI)

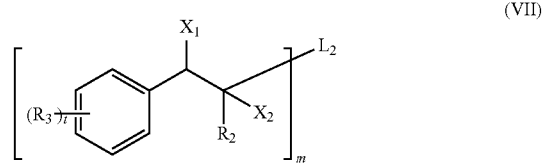

(VII)

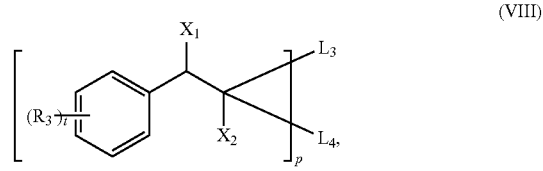

(VIII)

in the presence of an oxidative system comprising at least one bromide compound to form aryl ketones. $X_1$, $X_2$, $R_1$, $R_2$, $R_3$, $L_1$, $L_2$, $L_3$, $L_4$, t, n, m and p have the meanings as described in the specification and claims.

19 Claims, No Drawings

(56) References Cited

OTHER PUBLICATIONS

CN201610636058.4._English_translation_of_Search_Report.
Lixia Yin et al., "Oxidation of benzylie methylenes to ketones with Oxone-KBr in aqueous acetonitrile under transition metal free conditions"; Tetrahedron Letters, vol. 53; Dec. 12, 2012; pp. 4418-4421.
Katsuhiko Morivama et al., "Direct and Selective Benzylie Oxidation of Alkylarenes via C—H Abstraction Using Alkali Metal Bromides," Organic Letters, vol. 14; Issue 9; Dec. 31, 2012; pp. 2414-2417.
Shin-ichi Hirashim et al., "Aerobic photo-oxidation of alcohols in the presence of a catalytic inorganic promo source," Tetrahedron Letters: vol. 62: Dec. 31, 2006, pp. 7887-7891.

\* cited by examiner

PROCESS FOR PREPARING ARYL KETONE

RELATED APPLICATION

This application claims the benefit of U.S. Provisional Application No. 62/201,624 filed on Aug. 6, 2015, the entire contents of which are incorporated herein by reference.

FIELD OF THE INVENTION

The present invention relates to synthesis of aryl ketones. Specifically, the aryl ketones are suitable for use as a photoinitiator.

DESCRIPTION OF THE RELATED ART

Compounds of α-hydroxyketone class may be employed in many technical fields, one of them being the initiation of chemical reactions on irradiation. It has been known that some aryl hydroxyketone compounds are important photoinitiators for UV-radiation photopolymerizations of olefinically unsaturated systems.

Aryl hydroxyketone compounds can be prepared by Friedel-Crafts reactions. For example, as shown in the reaction scheme below, an aromatic compound is reacted with an acyl chloride in the presence of aluminum trichloride ($AlCl_3$) via Friedel-Crafts acylation and the obtained aryl ketone is then reacted with chlorine and treated with an alkaline to produce an aryl hydroxyketone:

Scheme 1

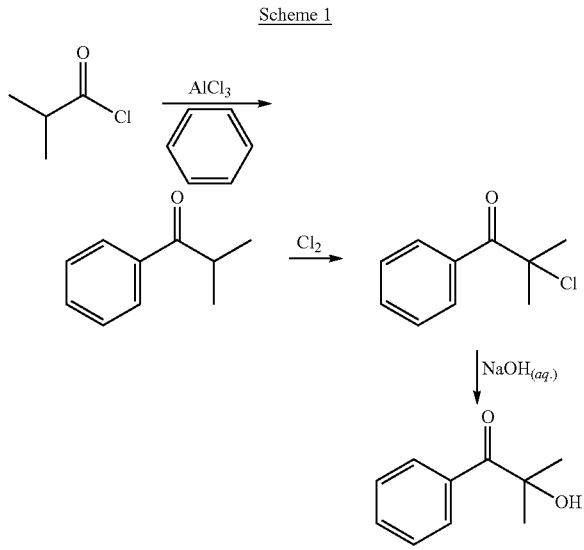

This reaction route, however, is complicated, involves several steps and several reactants, and causes the formation of many by-products. In addition, due to the physical and chemical properties of the reaction substance involved, chemical-resistant (especially acid-resistant) apparatus may be required, which raises the cost of equipments. Toxicity of the reaction substance, such as benzene and liquid chlorine, is another problem.

U.S. Pat. No. 8,252,959B2 and U.S. Pat. No. 8,575,394B2 discloses a process for the preparation of an 1,1-disubstituted oxirane. The oxirane may be converted into the corresponding α-hydroxyketone by subjecting to aerobic oxidation in the presence of a transition metal catalyst, for example, a Pd catalyst. Such process is not cost-efficient due to the use of expensive transition metal catalysts.

There is still need of a process for preparing aryl ketones and aryl hydroxyketones, which is more cost-efficient and environmentally-friendly.

BRIEF SUMMARY OF THE INVENTION

A process for preparing aryl ketone is disclosed, which in particular involves oxidation of α-position of a benzyl moiety of the reactant. The process of the present invention is simple, uses cheap and low toxic reagents so it is environmental-friendly and economically-efficient.

In the method of the present invention, the aqueous phase produced during the reaction can be recovered and reused after an optional post-treatment. Hence, materials can be effectively utilized and production costs can be lowered. In addition, the method of the present invention does not apply expensive heavy metals, so pollution to the environment can be avoided and production costs can be lowered. Further, by choosing proper reactant groups, the method of the present invention can even be conducted without any additionally-added organic solvents and achieves a higher reaction efficiency, yield and product purity. Not using a solvent means that the production costs can be lowered and waste can be reduced, and thus the method of the present invention is more environmentally friendly.

A one-pot process for preparing aryl ketone is also disclosed.

DETAILED DESCRIPTION OF THE INVENTION

In order to facilitate the understanding of the disclosure herein, terms are hereby defined below.

In the present invention, the term "about" refers to an acceptable deviation of a given value measured by a person of ordinary skill in the art, depending, in part, on how to measure or determine the value.

In the present invention, the term "alkyl" refers to a saturated, straight or branched alkyl, which comprises preferably 1-20 carbon atoms, and more preferably 1-16 carbon atoms. Examples of alkyl include, but are not limited to, methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, iso-heptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl or the like.

In the present invention, the term "cycloalkyl" as used herein means saturated or partially unsaturated cyclic carbon radicals containing 3 to 12 carbon atoms and more preferably 3 to 8 carbon atoms. Examples of cycloalkyl include, but are not limited to, cyclopropyl, cyclopropenyl, cyclobutyl, cyclopentyl, cyclohexyl, 2-cyclohexen-1-yl, and the like.

In the present invention, the term "aryl" or "aromatic" refers to a monocyclic, bicyclic or tricyclic aromatic ring system having 6 to 14 ring carbon atoms. Examples of aryl include, but are not limited to, phenyl, tolyl, naphthyl, fluorenyl, anthryl, phenanthrenyl and similar groups, among which phenyl and naphthyl are preferable.

In the present invention, the term "halogen" or "halo" denotes fluorine, chlorine, bromine or iodine, preferably bromine or chlorine.

In the present invention, the term "amido" refers to an optionally substituted group of the formula —C(O)NR'R" preferably having 1 to 20 carbon atoms, wherein R' and R" are substituents independently selected from hydrogen, alkyl, acyl, aryl, aralkyl, alkoxy, halogen, —OH, and the like. Preferably, R' and R" are independently optionally substituted alkyl or aryl groups.

In the present invention, the term "heterocycloalkyl" refers to cycloalkyl having at least one heteroatom selected from nitrogen, oxygen or sulfur in the ring structure wherein "cycloalkyl" has the meanings as described above. Examples of heterocycloalkyl include, but are not limited to, piperazinyl, pyrrolidinyl, dioxanyl, morpholinyl, and tetrahydrofuranyl.

In the present invention, the term "heteroaryl" refers aryl having at least one heteroatom selected from nitrogen, oxygen or sulfur in the ring structure. The ring structure may be monocyclic, bicyclic or tricyclic, optionally having fused rings, such as furan, thiophene, pyrrole, pyridine, bipyridine, picolylimine, γ-pyran, γ-thiopyran, phenanthroline, pyrimidine, bipyrimidine, pyrazine, indole, coumarone, thionaphthene, carbazole, dibenzofuran, dibenzothiophene, pyrazole, imidazole, benzimidazole, oxazole, thiazole, dithiazole, isoxazole, isothiazole, quinoline, bisquinoline, isoquinoline, bisisoquinoline, acridine, chromene, phenazine, phenoxazine, phenothiazine, triazine, thianthrene, purine, bisimidazole and bisoxazole.

In the present invention, the term "linking group" refers to a segment or group of molecules configured to connect two or more molecule to each another, which has a valency of 2, 3, 4, 5 or 6. The linking group of the present invention can be any suitable linking group which would not adversely affect the function of the desired aryl ketone. Examples include, but are not limited to, a direct bond, amine, amido, a di-, tri- tetra- penta- or hexa-valent aliphatic group, aromatic group, heteroaromatic group or heterocyclic-aliphatic group, or a di-, tri- tetra- penta- or hexa-valent group containing at least one S, P, O, N or Si atom. For example, the linking group having a valency of 2 may be a direct bond, alkylene, —O—, —S—,

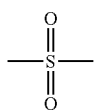

—NR'— (R' has the meanings as described above), —C(=O)—, phenylene, biphenylene, bisphenol group or a divalent linking group which contains any of the above radicals or a moiety derived from an aromatic heteroaromatic or heterocyclic-aliphatic compound.

Examples of tri-valent phenlyene can be

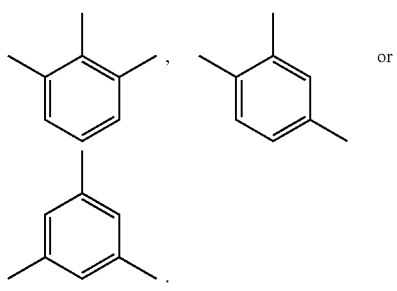

Examples of tetra-valent phenlyene can be

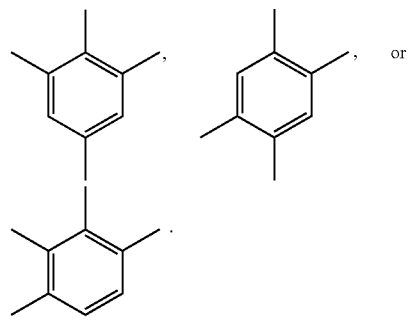

Examples of penta-valent phenlyene can be

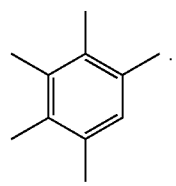

Examples of hexa-valent phenlyene can be

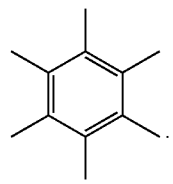

The term "nitrogen-linked" means that a substituent or linking group is linked with the main structure via the nitrogen atom within the substituent or linking group.

The groups in the compounds of the present invention may be optionally substituted, for example, unsubstituted or mono-, di- or tri substituted by suitable substituents, such as halogen, hydroxy, alkyl, alkoxy or aryl or the like, provided that the substituents would not significantly affect the efficacy of the present invention.

The present invention provides a process for preparing a compound of formula (I), (II), (III) or (IV):

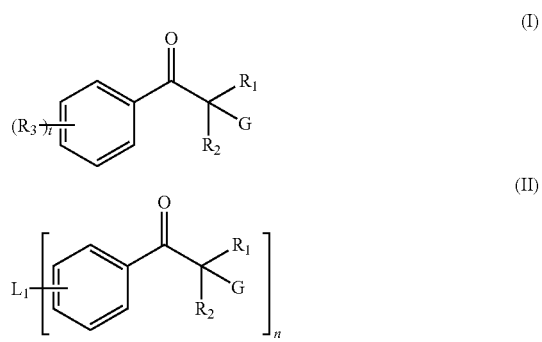

-continued

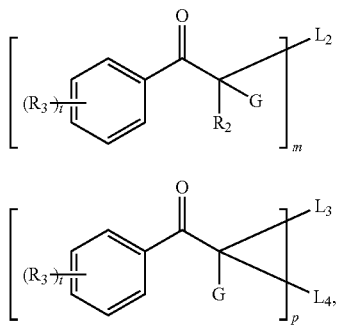

(III)

(IV)

which comprises photo-oxidizing a corresponding compound of formula (V), (VI), (VII) or (VIII):

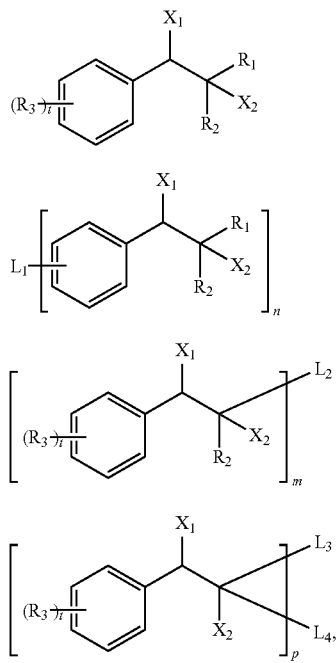

(V)

(VI)

(VII)

(VIII)

in the presence of an oxidative system comprising at least one bromide compound, wherein:

$X_1$ represents —H, halo, —OH or —$OR_4$;

$X_2$ represents —H, —OH, nitro, —$N(R_4)_2$, —$NHR_4$, —$R_4$, —$OR_4$, —$NR_4OH$, —$ONHR_4$, a 5- or 6-membered nitrogen-linked heterocyclyl having one or two heteroatoms selected from N, O or S in which at least one heteroatom is N, —$Si(R_4)_3$, —$OSi(R_4)_3$, —$P(R_4)_2$, —$P(=O)(OR_4)_2$ or —$P(=O)(R_4)_2$, with the proviso that when $X_1$ represents —OH, $X_2$ cannot be —OH or —$OR_4$;

$R_1$ and $R_2$ independently represent alkyl, cycloalkyl, heterocycloalkyl, aryl, heteroaryl, amino, amido, or an organic moiety comprising at least one of phosphor, oxygen, nitrogen and silicon, or $R_1$ and $R_2$, together with the carbon atom to which they attach, form a "—C=O" radical or a ring structure, which for example but is not limited cycloalkyl, heterocycloalkyl, aryl or heteroaryl, and preferably is $C_{3-8}$cycloalkyl (such as cyclopentyl or cyclohexyl);

$R_3$ represents H, alkyl, cycloalkyl, aryl, heteroaryl, amino or amido;

t represents an integer from 1 to 5;

G represents —H, halo, —OH, nitro, —$N(R_4)_2$, a 5- or 6-membered nitrogen-linked heterocyclyl having one or two heteroatoms selected from N, O or S, in which at least one heteroatom is N, —$NHR_4$, —$R_4$, —$OR_4$, —$NR_4OH$, —$ONHR_4$, —$Si(R_4)_3$, —$OSi(R_4)_3$, —$P(R_4)_2$, —$P(=O)(OR_4)_2$ or —$P(=O)(R_4)_2$;

$R_4$ represents alkyl or aryl;

n, m and p independently represent an integer from 2 to 6;

$L_1$ represents an n-valent linking group;

$L_2$ represents an m-valent linking group; and $L_3$ and $L_4$ represent a p-valent linking group and can be the same or different from each other, or $L_3$ and $L_4$, together with the carbon atom to which they attach, form a p-valent linking group.

The organic moiety comprising phosphor can be, for example, but is not limited to, alkylphosphines and arylphosphines; the organic moiety comprising oxygen can be, for example, but is not limited to, alcohols, alkoxides and ethers; the organic moiety comprising nitrogen can be, for example, but is not limited to, amines, nitriles and amides; the organic moiety comprises silicon can be, for example, but is not limited to, silanes and alkoxysilanes. In one preferred embodiment, the organic moiety comprising at least one of phosphor, oxygen, nitrogen or silicon may have any of the following formulae: —$OR_4$, —$NR_4OH$, —$ONHR_4$, —$Si(R_4)_3$, —$OSi(R_4)_3$, —$P(R_4)_2$, —$P(=O)(OR_4)_2$, —$P(=O)(R_4)_2$, —$N(R_4)_2$, a 5- or 6-membered nitrogen-linked heterocyclyl having one or two heteroatoms selected from N, O or S in which at least one heteroatom is N, —$R_5OR_4$, —$R_5NR_4OH$, —$R_5ONHR_4$, —$R_5Si(R_4)_3$, —$R_5OSi(R_4)_3$, —$R_5P(R_4)_2$, —$R_5P(=O)(OR_4)_2$, —$R_5P(=O)(R_4)_2$, —$R_5N(R_4)_2$, etc., where $R_4$ is as described above and $R_5$ represents a divalent linking group and is preferably alkylene or arylene.

G is preferably —H, halo, —OH, —$N(R_4)_2$, a 5- or 6-membered nitrogen-linked heterocyclyl having one or two heteroatoms selected from N, O or S in which at least one heteroatom is N, —$NHR_4$, —$R_4$ or —$OR_4$.

The linking group of $L_1$, $L_2$, $L_3$ and $L_4$ may have a valency of 2, 3, 4, 5 or 6, preferably a valency of 2, 3 or 4, more preferably a valency of 2 or 3, and most preferably a valency of 2. The linking group can be, for example, but is not limited to, a direct bond, or an aliphatic or aromatic linking group having a valency of 2, 3, 4, 5 or 6.

In one embodiment, the present invention provides a process for preparing aryl ketones from a compound of formula (V), (VI), (VII) or (VIII) where $X_1$ is —H and $X_2$ is —OH or —$OR_4$. Preferably, a compound of formula (V), (VI) or (VII) is used. More preferably, a compound of formula (V) is used.

In another embodiment, the present invention provides a process for preparing aryl ketones from a compound of formula (V), (VI), (VII) or (VIII) where $X_1$ is —OH. Preferably, a compound of formula (V), (VI) or (VII) is used. More preferably, a compound of formula (V) is used.

In a further embodiment, the present invention provides a process for preparing aryl ketones from a compound of formula (V), (VI), (VII) or (VIII) where $X_1$ is —H and $X_2$ is not —OH or —$OR_4$. Preferably, a compound of formula (V), (VI) or (VII) is used. More preferably, a compound of formula (V) is used.

In a further embodiment, the present invention provides a process for preparing aryl ketones from a compound of formula (V), (VI), (VII) or (VIII) where $X_1$ is —$OR_4$.

Preferably, a compound of formula (V), (VI) or (VII) is used. More preferably, a compound of formula (V) is used.

In a further embodiment, the present invention provides a process for preparing aryl ketones from a compound of formula (V), (VI), (VII) or (VIII) where $X_1$ is halo. Preferably, a compound of formula (V), (VI) or (VII) is used. More preferably, a compound of formula (V) is used.

In one embodiment, a compound of formula (VIII) where $L_3$ and $L_4$, together with the carbon atom to which they attach, form a p-valent linking group is used for preparing aryl ketones. In that case, $X_2$ is absent or is each independently a substituent attached to the linking group and has the definition described above.

In one embodiment of the present invention, the process for preparing an aryl ketone having formula (I), (II), (III) or (IV) comprises mixing a compound having formula (V), (VI), (VII) or (VIII) with peroxide and a bromide compound and then carrying out photo-oxidization reaction, provided that when $X_1$ is bromine, additional bromide compound(s) can be omitted. The sequence of adding starting materials (i.e., compound having formula (V), (VI), (VII) or (VIII), peroxide and a bromide compound) is not particularly limited and can be properly adjusted by a person of ordinary skill in the art based on the nature of the starting materials.

The process for preparing an aryl ketone having formula (I), (II), (III) or (IV) according to the present invention can be a one-pot process or a stepwise process. Stepwise processes are commonly used for synthesis and a person of ordinary skill in the art can select proper purification steps after each synthetic step so as to obtain a higher yield of intermediates and final products. On the other hand, one-pot processes allow for simpler and more economical operations. In the present invention, one-pot processes are preferred. The embodiments show that the one-pot processes according to the present invention may also result in a superior or comparable yield as compared to stepwise processes.

The process for preparing aryl ketones according to the present invention is described in detail below.

Route A

In a first aspect, the present invention provides a process for preparing aryl ketones via Route A.

In Route A, a compound of formula (V), (VI), (VII) or (VIII):

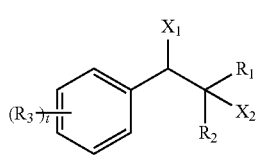 (V)

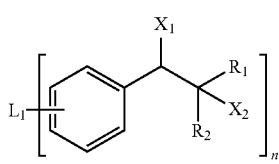 (VI)

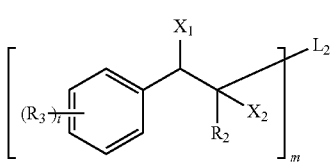 (VII)

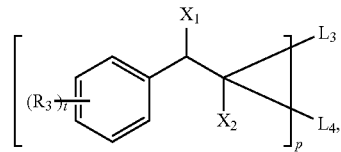 (VIII)

where $X_1$ is —H and $X_2$ is —OH or —OR$_4$, is photo-oxidized in the presence of an oxidative system comprising at least one bromide compound to obtain a corresponding compound of formula (I-1), (II-1), (II-1) or (IV-1):

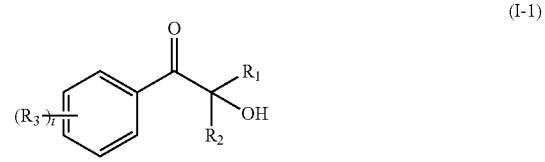 (I-1)

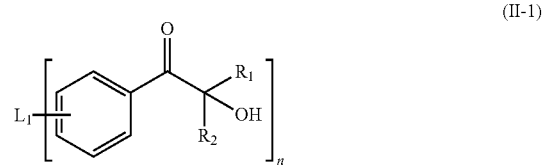 (II-1)

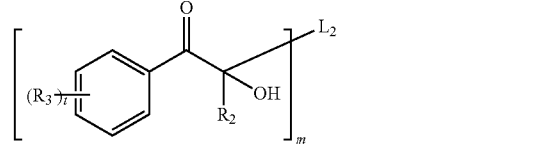 (III-1)

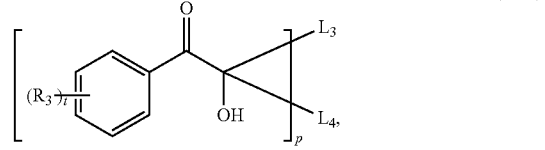 (IV-1)

$R_1$, $R_7$, $R_3$, $L_1$, $L_2$, $L_3$, $L_4$, t, n, m and p have the meanings as described above.

The compound of formula (V) may be commercially available or prepared from a compound of formula (IX) through an organic metal reaction:

 (IX)

wherein X is halo or lithium, preferably chlorine or bromine, and $R_3$ and t are as described above.

In particular, the organic metal reaction may be a Grignard reaction.

In one embodiment, the compound of formula (V) is obtained through an organic metal reaction by reacting a compound of formula (IX):

(IX)

$(R_3)_t$—⟨benzyl⟩—X with a compound of formula (X):

$$R_1C(=O)R_2 \quad (X)$$

in the presence of a suitable metal, such as magnesium, zinc or tin, to form the compound of formula (V), wherein $R_1$, $R_2$, $R_3$, and t are as described above and X is halo. The compounds of formulae (VI), (VII) and (VIII) may be prepared in a similar manner.

In one embodiment, the compound of formula (V) is obtained through an organic metal reaction by reacting a compound of formula (IX-1):

(IX-1)

$(R_3)_t$—⟨benzyl⟩—$CO_2R'$ with a compound of formula (X-1):

$$X—R_1 \quad (X-1),$$

and a compound of formula (X-2):

$$X—R_2 \quad (X-2),$$

in the presence of a suitable metal, such as magnesium, zinc or tin, to form the compound of formula (V), wherein $R_1$, $R_2$, $R_3$, and t are as described above, $R_1$ and $R_2$ can be the same or different from each other and preferably selected from alkyl, cycloalkyl and aryl, R' is alkyl, cycloalkyl or aryl, and X is halo. The compounds of formulae (VI), (VII) and (VIII) may be prepared in a similar manner.

Route A may be carried out in a one-pot process.

The process for preparing aryl ketones via Route A according to the present invention is further illustrated in detail by the example of one-pot process for oxidizing 2-methyl-1-phenylpropan-2-ol (compound 1) into 2-hydroxy-2-methyl-1-phenylpropan-1-one (ketone 1) provided below; however, the scope of the present invention is not limited thereto:

Compound 1 → Ketone 1

A one-pot process for oxidizing compound 1 into ketone 1 according to one embodiment of the present invention comprises the following steps:
  a) mixing compound 1 with peroxide (e.g., $H_2O_2$) to from a mixture;
  b) adding a bromine ($Br_2$) or a bromide compound solution (e.g., HBr) into the mixture of step (a); and
  c) adding more peroxide ($H_2O_2$) if needed and carrying out a photo-oxidization reaction (the formation of an organic layer and an aqueous layer can be observed after photo-oxidization reaction).

The sequence of adding peroxide and a bromide compound (e.g. bromine or a bromide compound solution as stated above) is not particularly limited. For example, in an alternative embodiment of the present invention, the one-pot process for oxidizing compound 1 into ketone 1 may comprise by the following steps:
  a) mixing compound 1 with bromine or a bromide compound solution (e.g., HBr) to form a mixture;
  b) adding peroxide (e.g., $H_2O_2$) into the mixture of step (a); and
  c) adding more peroxide ($H_2O_2$) if needed and carrying out a photo-oxidization reaction (the formation of an organic layer and an aqueous layer can be observed after photo-oxidization reaction).

If needed, an organic solvent, such as nonpolar solvent (e.g., cyclohexane) and halogenated hydrocarbons (e.g., dichloromethane (DCM) or dichloroethane (DCE)), can be used in either of the steps (a) and (b) or both.

In step c), the photo-oxidization reaction can be carried out at a temperature between about −10° C. and about 100° C., preferably about 0° C. to 80° C., more preferably from 20° C. to 80° C., with light radiation having between about 380 and about 760 nm. The formation of an organic layer and an aqueous layer can be observed after photo-oxidization reaction while ketone 1 is in the organic layer.

After carrying out the above steps a) to c) in the one-pot process, the product, ketone 1, can be purified by any suitable methods, for example, by extraction and/or evaporation. The solvent added for extraction is not particularly limited as long as it is useful for the extraction of ketone 1, which can be, for example, but is not limited to DCE, brine, water or a combination thereof. In one embodiment of the present invention, DCE and brine are added to the solution of step c), the solution is vigorously stirred for 30 minutes and stands for another 30 minutes, and then, the organic layer is decanted. Ketone 1 is obtained by removing the solvent from the decanted organic layer via evaporation. If necessary, ketone 1 can be further purified, for example, by distilling, liquid chromatography (LC) or high performance liquid chromatography (HPLC).

The process for preparing aryl ketones via Route A may also be carried out in a stepwise process (i.e., a non-one-pot process). The steps in such a stepwise process may be the same as those in a one-pot process. The stepwise process may comprise a further photo-oxidization, separation and/or purification step so as to improve the purity or yield of the desired product. For example, a stepwise process for oxidizing compound 1 into ketone 1 according to one embodiment of the present invention comprises the following steps:
  a) mixing compound 1 with peroxide (e.g., $H_2O_2$) to from a mixture;
  b) adding bromine or a bromide compound solution (e.g., HBr) into the mixture of step (a);
  c) adding more peroxide ($H_2O_2$) if needed and carrying out a photo-oxidization reaction (the formation of an organic layer and an aqueous layer can be observed after photo-oxidization reaction);
  d) separating the organic layer from the aqueous layer;
  e) removing the organic solvent from the separated organic layer, for example, by heating with a water bath at a temperature between about 80° C. and about 120° C.;
  f) adding water and more peroxide ($H_2O_2$), if needed, to the product of step e) and carrying out a further photo-oxidization reaction (the formation of an organic layer and an aqueous layer can be observed after photo-oxidization reaction); and Similar to the one-pot process, if needed, an organic solvent, such as nonpolar solvent (e.g., cyclohexane) and halogenated hydrocarbons (e.g., dichloromethane (DCM) or dichloroethane (DCE)), can be used in either of the steps (a) and (b) or both in the non-one-pot process.

The photo-oxidization reaction in steps c) and f) can be carried out at a temperature between about −10° C. and about 100° C., preferably about 0° C. to 80° C., with light radiation having between about 380 and about 760 nm. The formation of an organic layer and an aqueous layer can be observed after photo-oxidization reaction. Ketone 1 is in the organic layer after the photo-oxidization reaction of step f).

Similar to the one-pot process, after carrying out the above steps a) to f) in the non-one-pot process, the product, ketone 1, can be purified by any suitable methods as described above.

As an alternative embodiment, the addition order of bromine or a bromide compound solution and peroxide in steps a) and b) can be interchanged.

Route B

In a second aspect, the present invention provides a process for preparing aryl ketones via Route B.

In Route B, a compound of formula (V), (VI), (VII) or (VIII):

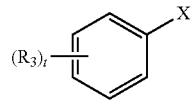 (V)

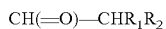 (VI)

(VII)

(VIII)

where $X_1$ is —OH, is photo-oxidized in the presence of an oxidative system comprising at least one bromide compound to obtain a corresponding compound of formula (I), (II), (III) or (IV):

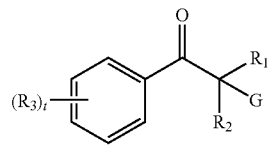 (I)

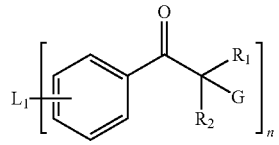 (II)

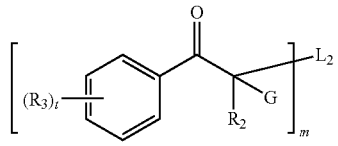 (III)

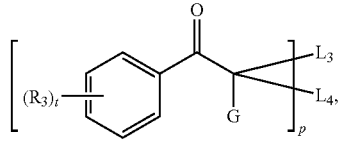 (IV)

$R_1$, $R_2$, $R_3$, $L_1$, $L_2$, $L_3$, $L_4$, $X_2$, G, t, n, m and p have the meanings as described above.

In one embodiment, the compound of formula (V) is obtained through an organic metal reaction by reacting a compound of formula (IX'):

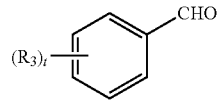 (IX')

with a compound of formula (X'):

CH(=O)—CHR$_1$R$_2$ (X')

in the presence of a suitable metal, such as magnesium, zinc or tin, to form the compound of formula (V), wherein $R_1$, $R_2$, $R_3$, and t are as described above and X is halo. The compounds of formulae (VI), (VII) and (VIII) may be prepared in a similar manner.

In one embodiment, the compound of formula (V) is obtained through an organic metal reaction by reacting a compound of formula (IX"):

 (IX")

with a compound of formula (X"):

X—CHR$_1$R$_2$ (X")

in the presence of a suitable metal, such as magnesium, zinc or tin, to form the compound of formula (V), wherein $R_1$, $R_2$, $R_3$, and t are as described above and X is halo. The compounds of formulae (VI), (VII) and (VIII) may be prepared in a similar manner.

Route B may be carried out in either a one-pot process or a non-one-pot process.

The amount of the bromide compound used in Route B is not particularly limited and can be an equivalent amount or a catalytic amount.

In one specific embodiment for the method of preparing aryl ketones via Route B of the present invention, when a bromide compound is used in a catalytic amount, a corresponding compound of formula (I), (II), (III) or (IV) can be produced. In one example of such, a compound of formula (V), (VI), (VII) or (VIII) where $X_2$ represents —H is used and G in the corresponding compound of formula (I), (II), (III) or (IV) is —H.

In another specific embodiment for the method of preparing aryl ketones via Route B of the present invention, when a bromide compound is used more than an equal equivalence of (e.g., in an amount of 1.1 equivalent), a corresponding compound of formula (I), (II), (III) or (IV) where G represents —Br can be produced if $X_2$ in the compound of formula (V), (VI), (VII) or (VIII) is a group capable of being substituted by bromine.

Route C

In a third aspect, the present invention provides a process for preparing aryl ketones via Route C.

In Route C, a compound of formula (V), (VI), (VII) or (VIII):

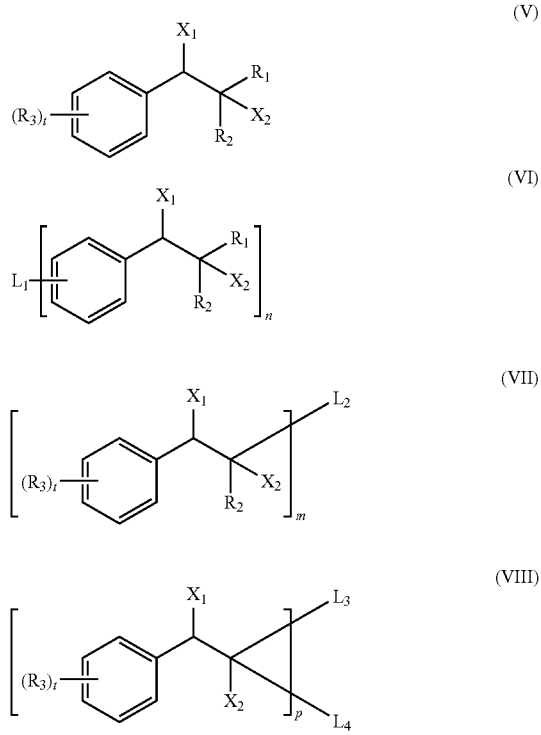

where $X_1$ is —H and $X_2$ is not —OH or —$OR_4$, is photo-oxidized in the presence of an oxidative system comprising at least one bromide compound to obtain a corresponding compound of formula (I), (II), (III) or (IV):

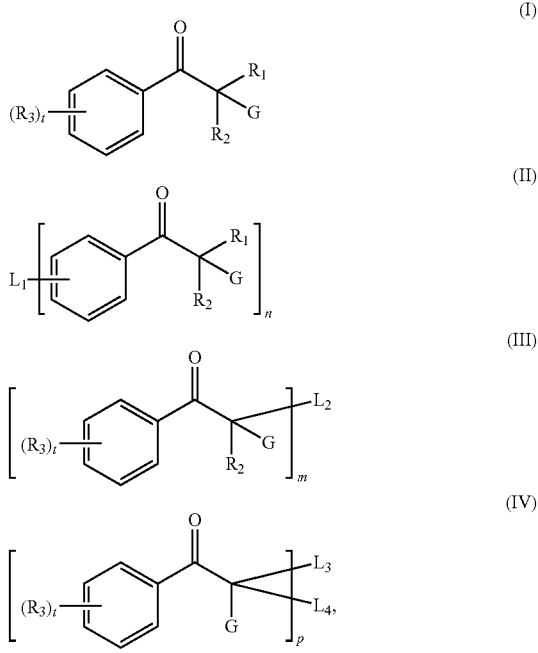

$R_1$, $R_2$, $R_3$, $L_1$, $L_2$, $L_3$, $L_4$, G, t, n, m and p have the meanings as described above; $X_2$ has the meanings as described above but is not —OH or —$OR_4$.

Route C may be carried out in a one-pot process.

The process for preparing aryl ketones via Route C according to the present invention is further illustrated in detail by the example of one-pot processes for oxidizing isobutylbenzene (compound 2) into 2-methyl-1-phenylpropan-1-one (ketone 2) provided below; however, the scope of the present invention is not limited thereto:

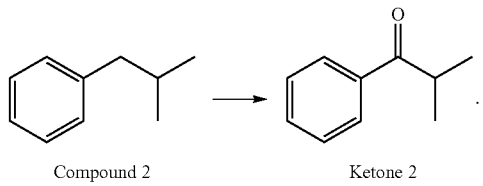

Compound 2                    Ketone 2

A one-pot process for oxidizing compound 2 into ketone 2 according to one embodiment of the present invention may comprises the following steps:
 a) mixing compound 2 with peroxide (e.g., $H_2O_2$) to form a mixture;
 b) adding bromine or a bromide compound solution (e.g., HBr) into the mixture of step (a); and
 c) adding more peroxide ($H_2O_2$) if needed and carrying out a photo-oxidization reaction (the formation of an organic layer and an aqueous layer can be observed after photo-oxidization reaction).

Similar to Route A, the sequence of adding peroxide and a bromide compound in Route C is not particularly limited. For example, in an alternative embodiment of the present invention, the one-pot process for oxidizing compound 2 into a ketone 2 may comprise the following steps:
 a) mixing compound 3 with bromine or a bromide compound solution (e.g., HBr) to from a mixture;
 b) adding a peroxide (e.g., $H_2O_2$) into the mixture of step (a); and c) adding more peroxide ($H_2O_2$) if needed and carrying out a photo-oxidization reaction (the formation of an organic layer and an aqueous layer can be observed after photo-oxidization reaction).

Similar to Route A, if needed, an organic solvent, such as nonpolar solvent (e.g., cyclohexane) and halogenated hydrocarbons (e.g., dichloromethane (DCM) or dichloroethane (DCE)), can be used in either of the steps (a) and (b) or both.

Similar to Route A, in step c), the photo-oxidization reaction can be carried out at a temperature between about −10° C. and about 100° C., preferably about 0° C. to 80° C., more preferably from 20° C. to 80° C., with light radiation having between about 380 and about 760 nm. The formation of an organic layer and an aqueous layer can be observed after photo-oxidization reaction while ketone 2 is in the organic layer.

The product, ketone 2, can be purified or further purified by any suitable methods as described above for Route A. In one embodiment of the present invention, DCE and brine are used for extraction of ketone 2.

Similar to Route A, the process for preparing aryl ketones via Route C may also be carried out in a stepwise process. The steps in such a stepwise process may be the same as those in a one-pot process. The stepwise process may comprise a further photo-oxidization, separation and/or purification steps so as to improve the purity or yield of the desired product.

Route D

In a fourth aspect, the present invention provides a process for preparing aryl ketones via Route D.

In Route D, a compound of formula (V), (VI), (VII) or (VIII):

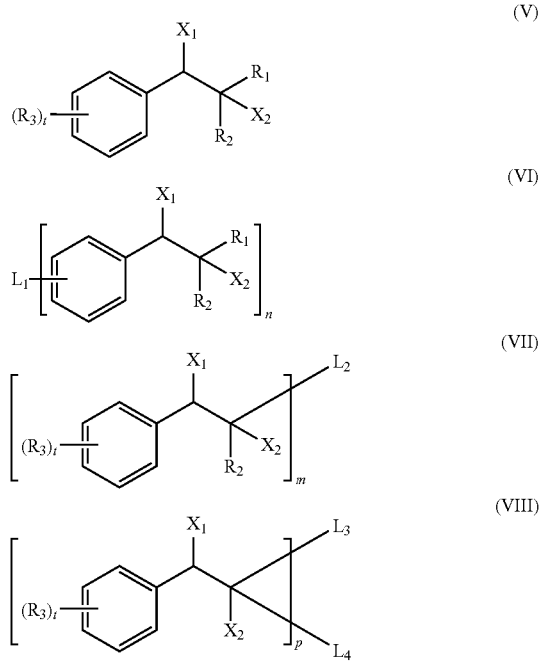

where $X_1$ is —$OR_4$, is photo-oxidized in the presence of an oxidative system comprising at least one bromide compound to obtain a corresponding compound of formula (I), (II), (III) or (IV):

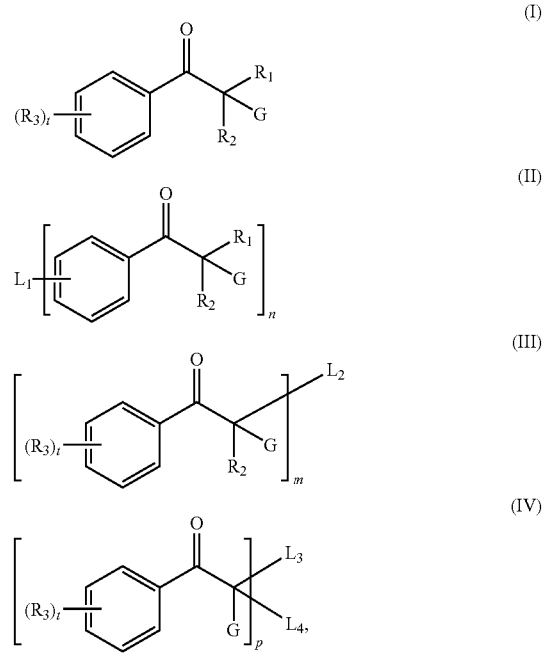

$R_1$, $R_2$, $R_3$, $L_1$, $L_2$, $L_3$, $L_4$, $X_2$, G, t, n, m and p have the meanings as described above.

Route D may be carried out in a one-pot process.

The process for preparing aryl ketones via Route D according to the present invention is further illustrated in detail by the example of a one-pot process for oxidizing (1-ethoxy-2-methyl-propyl)benzene (compound 3) into 2-methyl-1-phenylpropan-1-one (ketone 2) provided below; however, the scope of the present invention is not limited thereto:

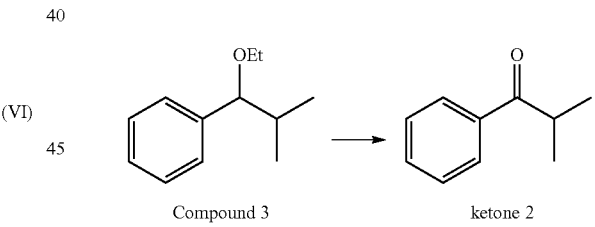

A one-pot process for oxidizing compound 3 into ketone 2 according to one embodiment of the present invention may comprises the following steps:

a) mixing compound 3 with peroxide (e.g., $H_2O_2$) to form a mixture;

b) adding bromine or a bromide compound solution (e.g., HBr) into the mixture of step (a); and c) adding more peroxide ($H_2O_2$) if needed and carrying out a photo-oxidization reaction (the formation of an organic layer and an aqueous layer can be observed after photo-oxidization reaction).

Similar to Route A, the sequence of adding peroxide and a bromide compound in Route D is not particularly limited. For example, in an alternative embodiment of the present invention, the one-pot process for oxidizing compound 3 into a ketone 2 may comprise the following steps:

a) mixing compound 3 with bromine or a bromide compound solution (e.g., HBr) to from a mixture;
b) adding a peroxide (e.g., $H_2O_2$) into the mixture of step (a); and
c) adding more peroxide ($H_2O_2$) if needed and carrying out a photo-oxidization reaction (the formation of an organic layer and an aqueous layer can be observed after photo-oxidization reaction).

Similar to Route A, if needed, an organic solvent, such as nonpolar solvent (e.g., cyclohexane) and halogenated hydrocarbons (e.g., dichloromethane (DCM) or dichloroethane (DCE)), can be used in either of the steps (a) and (b) or both.

Similar to Route A, in step c), the photo-oxidization reaction can be carried out at a temperature between about −10° C. and about 100° C., preferably about 0° C. to 80° C., more preferably from 20° C. to 80° C., with light radiation having between about 380 and about 760 nm. The formation of an organic layer and an aqueous layer can be observed after photo-oxidization reaction while ketone 2 is in the organic layer.

The product, ketone 2, can be purified or further purified by any suitable methods as described above for Route A. In one embodiment of the present invention, water is used for extraction of ketone 2.

Similar to Route A, the process for preparing aryl ketones via Route D may also be carried out in a stepwise process. The steps in such a stepwise process may be the same as those in a one-pot process. The stepwise process may comprise a further photo-oxidization, separation and/or purification steps so as to improve the purity or yield of the desired product.

Route E

In a fifth aspect, the present invention provides a process for preparing aryl ketones via Route E.

In Route E, a compound of formula (V), (VI), (VII) or (VIII)

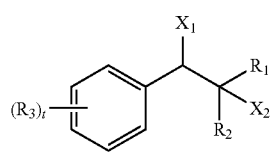
(V)

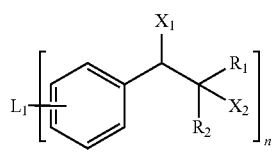
(VI)

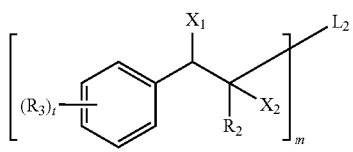
(VII)

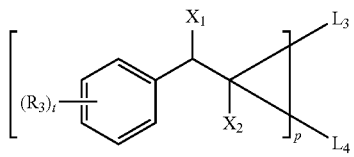
(VIII)

where $X_1$ is halo, is photo-oxidized in the presence of an oxidative system comprising at least one bromide compound to obtain a corresponding compound of formula (I), (II), (III) or (IV):

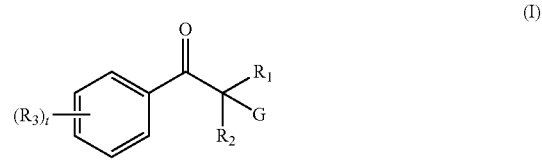
(I)

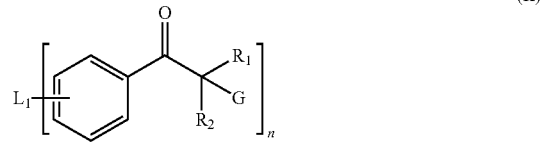
(II)

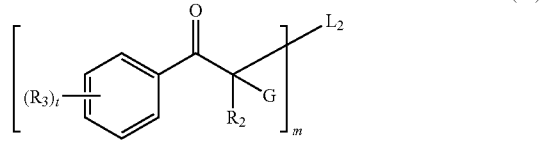
(III)

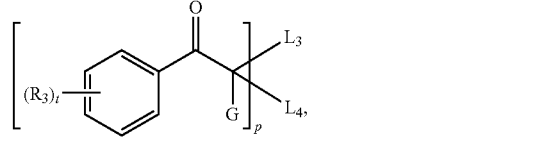
(IV)

$R_1$, $R_2$, $R_3$, $L_1$, $L_2$, $L_3$, $L_4$, $X_2$, G, t, n, m and p have the meanings as described above.

Route E may be carried out in a one-pot process.

In the embodiment where $X_1$ in the compound of formula (V), (VI) (VII) or (VIII) is bromine, the compound of formula (V), (VI) (VII) or (VIII) itself acts as a bromide compound of the oxidative system, and therefore, the addition of a bromide compound can be omitted. In the embodiment where $X_1$ in the compound of formula is halo other than bromine, a bromide compound should be added. The sequence of adding peroxide and a bromide compound in Route D is not particularly limited and is similar to that in other routes.

The process for preparing aryl ketones via Route E according to the present invention is further illustrated in detail by the example of one-pot processes for oxidizing (1-bromo-2-methylpropyl)benzene (compound 4) into 2-methyl-1-phenylpropan-1-one (ketone 2) provided below; however, the scope of the present invention is not limited thereto:

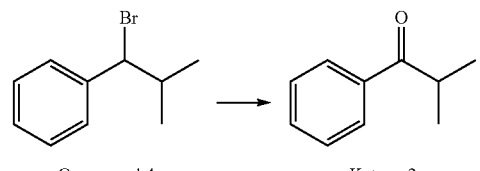

Compound 4    Ketone 2

A one-pot process for oxidizing compound 4 into ketone 2 according to one embodiment of the present invention comprises the following steps:

a) mixing compound 4 with a peroxide (e.g., $H_2O_2$) to prepare a mixture; and
b) adding more peroxide ($H_2O_2$) if needed and carrying out a photo-oxidization reaction (the formation of an organic layer and an aqueous layer can be observed after photo-oxidization reaction).

In one preferred embodiment, the process for oxidizing compound 4 into ketone 2 can be carried out in the presence of water. The sequence of adding water in Route E is not particularly limited, i.e., water can be added in either of the steps (a) and (b) or both. In one preferred embodiment, water is in an excess amount as compared to the molar amount of Compound 4.

Similar to Route A, if needed, an organic solvent, such as nonpolar solvent (e.g., cyclohexane) and halogenated hydrocarbons (e.g., dichloromethane (DCM) or dichloroethane (DCE)), can be used in either of the steps (a) and (b) or both.

Similar to Route A, in step c), the photo-oxidization reaction can be carried out at a temperature between about −10° C. and about 100° C., preferably about 0° C. to 80° C., more preferably from 20° C. to 80° C., with light radiation having between about 380 and about 760 nm. The formation of an organic layer and an aqueous layer can be observed after photo-oxidization reaction while ketone 2 is in the organic layer.

The product, ketone 2, can be purified or further purified by any suitable methods as described above for Route A. In one embodiment of the present invention, DCE and brine is used for extraction of ketone 2.

The step f) as described in the Route A (the stepwise process) can be also independently referred to as Route E.

Similar to Route A, the process for preparing aryl ketones via Route E also may be carried out in a stepwise process which may contain a further photo-oxidization, separation and/or purification steps.

The moiety

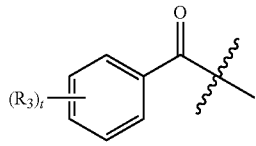

in formula (I), (III) or (IV) is equal to:

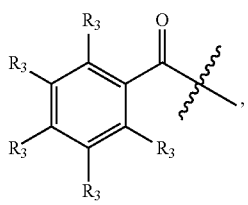

wherein $R_3$ is as described above and preferably hydrogen.

In the present invention, the compound of formula (II) may have any of the following structure:

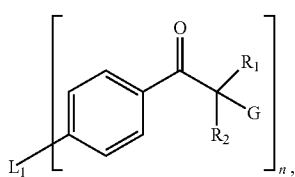

(II')

-continued

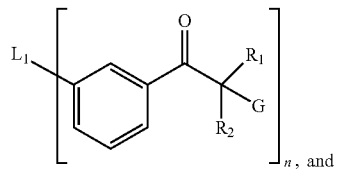

(II″)

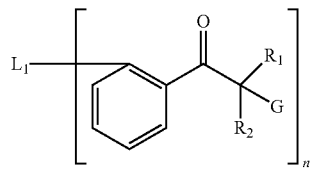

(II‴)

wherein $R_1$ $R_2$, G, $L_1$ and n are as described above.

In one embodiment, $R_1$ and $R_2$ independently represent $C_{1-3}$alkyl, and G is —Br or —OH in the above-mentioned reaction routes.

In another embodiment, $R_1$ and $R_2$, together with the carbon atom to which they attach, form cycloalkyl, preferably $C_{3-8}$cycloalkyl (such as cyclopentyl or cyclohexyl), and G is —Br or —OH in the above-mentioned reaction routes.

The term "oxidative system" refers to any substance or combination thereof capable of oxidizing the reactants in any of the above-mentioned reaction routes. The oxidative system of the present invention includes halogens, peroxides, or any substance that can form an oxidizing agent in situ. Specifically, the oxidative system of the present invention comprises at least one bromide compounds and an optional compatible oxidizing agents or precursors. In one preferred embodiment, in addition to bromide compounds, the oxidative system of the present invention further comprises one or more peroxides.

The term "equivalent" refers to the molar ratio of a designated component to the group(s) to be reacted in a reactant. For example, in a photo-oxidation reaction, the equivalent of a bromide compound, a peroxide or an acid is the molar ratio of said component to $X_1$ in a compound of formula (V), (VI), (VII) or (VIII). An equal equivalent means that the molar amount of the designated component equals to that of the group(s) to be reacted in a reactant.

The term "catalytic amount" refers to an equivalent of a designated component which is capable of catalyzing the photo-oxidation reaction (generally, a catalytic amount is less than an equal equivalent). The catalytic amount depends on the nature of the reactants and the designated component.

The term "bromide compound" refers to elemental bromine existing as a diatomic molecule (i.e., $Br_2$) or a compound having bromine element(s). The compound having bromine element(s) can be, for example, but is not limited to, hydrogen bromide (HBr), a hypobromite compound (e.g., HOBr) or a metal bromide having the formula of $M(Br)_k$, wherein M is a metal ion selected from an alkali metal or an alkaline earth metal and k equals to the valency of M.

In the present invention, the amount of a bromide compound used for photo-oxidation generally ranges from 0.05 to 2 equivalent. Persons of ordinary skill in the art can adjust the amount based on the demand in an actual reaction. For example, in one preferred embodiment of the present invention, Routes A and C can be conducted at the condition where the bromide compound of the oxidative system is present in an amount of larger than 1 equivalent and products having higher purity can be obtained. According to another preferred embodiment of the present invention, Routes B, D and E can be conducted at the condition where a bromide compound of the oxidative system is present in an amount of less than or equal to 1 equivalent, preferably from 0.05 to 0.8 equivalent and more preferably from 0.3 to 0.5 equivalent. In other words, the method via Route B, D or E of the present invention can be conducted when the bromide compound in the oxidative system is in a catalytic amount (less than 1 equivalent).

The term "peroxide" refers to a compound containing an oxygen-oxygen single bond or the peroxide anion, $O_2^{2-}$. Examples of the peroxide include, but are not limited to, hydrogen peroxide ($H_2O_2$), sodium peroxide ($Na_2O_2$), potassium peroxide ($K_2O_2$), calcium peroxide ($CaO_2$), magnesium peroxide ($MgO_2$), zinc peroxide ($ZnO_2$), strontium peroxide ($SrO_2$) and organic peroxides, such as ethaneperoxoic acid or the like. The peroxide can be used in an amount from 0.2 to 5 equivalent, preferably 0.5 to 3 equivalent and more preferably 0.8 to 2 equivalent.

Accordingly, Examples of the oxidative system comprise $Br_2$, $Br_2/H_2O_2$, $HBr/H_2O_2$, $HBr/Cl_2$, bromide/acid/$H_2O_2$, bromide/chlorine, HBr/halogen acid (e.g., HCl), HBr/hypohalite, bromide/acid/halide salt, bromide salt/acid/$H_2O_2$ and bromide/acid/hypohalite. The acid is preferably selected from sulfuric acid, hydrochloric acid, hydrobromic acid, nitric acid, phosphoric acid, acetic acid, hydroiodic acid and any combination thereof. The acid can be used in an amount from 1 to 1.5 equivalent. The hypohalite is preferably HOBr. The halide salt is not particularly limited and preferably selected from NaBr, KBr, NaI, NaBr and any combination thereof.

In one preferred embodiment, the oxidative system is used together with a light radiation to enhance the reaction rate or yield. The light radiation may have a wavelength in the range of about 380 to about 760 nm The temperature of the photo-oxidation is preferable, but not limited, from about −10 to about 100° C., preferably from about 0° C. to about 80° C., and more preferably from 20° C. to 80° C.

The reaction medium of the photo-oxidation may be a homogeneous system or a heterogeneous system. The term "homogeneous system" refers to a system that a reaction is conducted in the same phase, such as between two or more miscible liquids. The term "heterogeneous system" refers to a system that a reaction is conducted in different phases, such as purging a reactant gas into a solution comprising other reactant or between immiscible liquids.

The reaction medium can be a solution or a dispersion, optionally at agitation, heating and/or refluxing. The solvents used for the solution or dispersion may comprise halogenated aliphatic hydrocarbons, halogenated aromatic hydrocarbons, aliphatic hydrocarbons, aromatic hydrocarbons, esters, alcohols, ethers, nitrile type solvents, sulfoxide type solvents, (N-substituted)formamide type solvents, water, or a solvent mixture composed of the above. The solvents are preferably aliphatic hydrocarbons (e.g., alkane or cycloalkane), halogenated aliphatic hydrocarbons (e.g., alkane or cycloalkane substituted by halo atom(s)), halogenated aromatic hydrocarbons, esters, alcohols, ethers (e.g., tetrahydrofuran (THF)), sulfoxide type solvents (e.g., dimethyl sulfoxide (DMSO)), (N-substituted)formamide type solvents (e.g., formamide and dimethylformamide (DMF)) or a combination thereof, and are more preferably cyclohexane, dichloromethane (DCM), dichloroethane (DCE), ethanol, THF, DMSO, DMF or a combination thereof.

In one embodiment, during photo-oxidation, a corresponding compound of formula (I), (II), (III) or (IV) (where G represents H) can be formed from a compound of formula (V), (VI), (VII) or (VIII) where $X_1$ and $X_2$ both represent —H and the compound of formula (I), (II), (III) or (IV) can then be further reacted with a chlorine, bromine or iodine compound and hydrolyzed to obtain a final product where G represents —OH.

In another embodiment, when a compound of formula (I), (II), (III) or (IV) where G is halo, preferably bromide, is obtained from a method of the present invention, the compound of formula (I), (II), (III) or (IV) may be respectively converted to a compound of formula (I-1), (II-1), (III-1) or (IV-1) in the presence of a base:

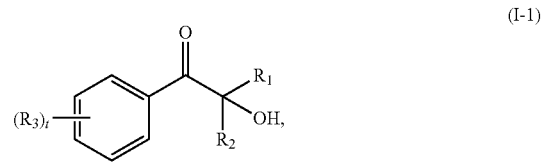

(I-1)

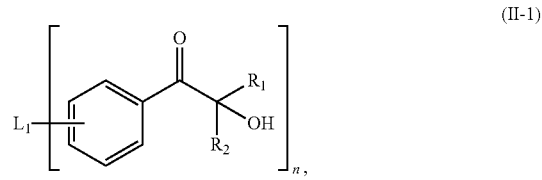

(II-1)

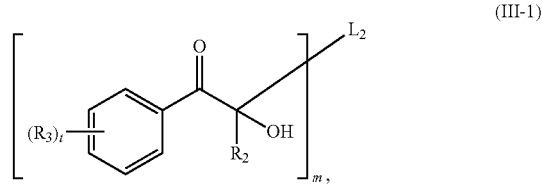

(III-1)

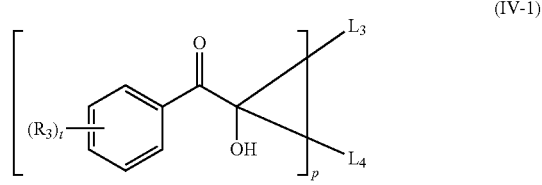

(IV-1)

wherein $R_1$, $R_2$, $R_3$, $L_1$, $L_2$, $L_3$ and $L_4$, t, n, m, p are as described above. Preferably, the base is $M(OH)_k$, wherein M is a metal ion selected from alkali metals or alkaline earth metals and k equals to the valency of M. In this embodiment, only a few by-products are produced, and therefore, the bromide compound (for example, HBr) of the oxidative system, which has reacted with the compound of formula (V) (VI), (VII) or (VIII) during photo-oxidization, can be effectively recycled by substituting —Br part of the compound of formula (V) (VI), (VII) or (VIII) with —OH part of the base (for example, NaOH)

The process according to the present invention involves simple steps, uses cheaper reagents with lower toxicity and thus are more cost-efficient and environmentally-friendly as compared to prior art techniques. In addition, the process according to the present invention can be carried out as a one-pot process with a superior or comparable yield, such that the operation becomes much simpler and the cost can be further reduced.

In most cases (e.g., the final product does not possess additional bromine when compared with the initial reactant), the bromide compound in the oxidative system of the present invention will exist in the aqueous phase when the reaction is completed, and thus the aqueous phase has photo-oxidation reactivity and can be reused as an oxidative system in a further photo-oxidation reaction. In this aspect, the aqueous phase can be directly used or subjected to treatment prior to being used. The treatment can be such as concentration (e.g., removal of water), addition of peroxide or an acid, etc. Hence, the method of the present invention has another advantage that the photo-oxidation reaction can be continuously conducted with little or no loss of the bromide compound and thereby achieving the effects of significantly reducing material costs and being environmentally friendly.

In addition, in preferred embodiments (in particular the methods via Route C or E), the method for preparing aryl ketones of the present invention may be conducted without additionally-added organic solvent. This is advantageous for reducing the cost of reactants and the amount of reaction wastes and improving yield and purity of the products.

The processes for preparing aryl ketones are exemplified by the following examples, which do not intend to limit the scope of the present invention.

EXAMPLES

Example 1

Synthesis of
2-hydroxy-2-methyl-1-phenylpropan-1-one

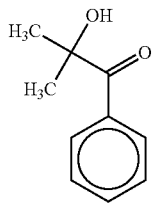

Preparation of 2-methyl-1-phenylpropan-2-ol 171 g (1 mol) of benzyl bromide was slowly added into 36.5 g (1.5 mol) of magnesium powder in 500 g of dry THF to form a first mixture. The first mixture was gently heated to 50° C. and stirred for 1 hour, and then 69.7 g (1.2 mol) of anhydrous acetone was slowly added to form a second mixture. The second mixture was heated to reflux for 8 hours. After cooling to room temperature, 1000 g of 10% hydrochloric acid was added, and the resulting mixture was extracted with 500 g of dichloromethane twice. Upon separation of the phases, the organic layer was dried with a desiccant (magnesium sulfate). A colorless liquid, 2-methyl-1-phenylpropan-2-ol, with a yield of 95% was obtained after the removal of desiccant and solvent from the organic layer.

Synthesis of
2-hydroxy-2-methyl-1-phenylpropan-1-one 111.8 g (0.7415 mol) of 2-methyl-1-phenylpropan-2-ol and 56 g (0.82 mol) of 50% hydrogen peroxide were mixed in 1000 g of dichloroethane to form a mixture. 252 g (1.5 mol) of hydrobromic acid was slowly added into the mixture under ice bath (0° C.), and then the mixture was irradiated by a visible light lamp (with a wavelength of about 400 nm) for 8 hours to form a crude product (in an organic layer). 1-bromo-2-methyl-1-phenylpropan-2-ol was produced with a yield of 95% after removing the solvent from the crude product by evaporation.

Next, 600 g of water was mixed with 162 g (0.7 mol) of 1-bromo-2-methyl-1-phenylpropan-2-ol. The mixture was stirred at 100° C. for 1 hour and then cooled to room temperature. 76 g (1.11 mol) of 50% hydrogen peroxide was slowly added into the mixture under ice bath, and then the mixture was irradiated by a visible light lamp (with a wavelength of about 400 nm) for 6 hours to form a crude product (in an organic layer). After extracted the crude product with DCE and brine and evaporated to remove the solvent, 2-hydroxy-2-methyl-1-phenylpropan-1-one was produced with a yield of 82%. (bp. 102-103° C./4 mmHg)

Example 2

One-Pot Method for Synthesizing
2-hydroxy-2-methyl-1-phenylpropan-1-one

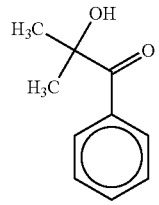

112 g (0.745 mol) of 2-methyl-1-phenylpropan-2-ol and 127 g (1.86 mol) of 50% hydrogen peroxide were mixed in 1000 g of DCE to form a mixture. 63 g (0.373 mol) of hydrobromic acid was slowly added to the mixture at 60° C., and then mixture was irradiated by a visible light lamp (with a wavelength of about 400 nm) for 12 hours to form a crude product (in an organic layer). After extracted the curde product with DCE and brine and evaporated to remove the solvent, 2-hydroxy-2-methyl-1-phenylpropan-1-one was obtained with a yield of 85%. (bp. 102-103° C./4 mmHg)

Example 3

Synthesis of
(1-hydroxycyclohexyl)-phenylmethanone

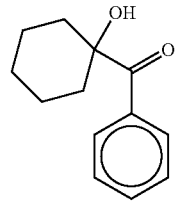

Preparation of 1-benzylcyclohexan-1-ol 171 g (1 mol) of benzyl bromide was slowly added into 36.5 g (1.5 mol) of magnesium powder in 500 g of dry THF to form a first mixture. The first mixture was gently heated to 60° C. and stirred for 1 hour, and then 117.8 g (1.2 mol) of anhydrous cyclohexanone was slowly added to form a second mixture. The second mixture was heated to reflux for 8 hours. After cooling to room temperature, 1000 g of 10% hydrochloric acid was added, and the resulting mixture was extracted with 500 g of dichloromethane twice, Upon separation of the phases, the organic layer was dried with a desiccant (magnesium sulfate). A colorless liquid, 1-benzyl-cyclohexan-1-ol, with a yield of 90% was obtained after the removal of desiccant and solvent from the organic layer.

Synthesis of
(1-hydroxycyclohexyl)-phenyl-methanone 141.8 g (0.745 mol) of i-benzylcyclohexan-1-ol and 56 g (0.82 mol) of 50% hydrogen peroxide were mixed in 1000 g of DCE to form a mixture. 252 g (1.5 mol) of hydrobromic acid was slowly added into the mixture under ice bath, and then the mixture was irradiated by a visible light lamp (with a wavelength of about 400 nm) for 8 hours to form a crude product. (1-hydroxycyclohexyl) benzyl bromide, was produced with a yield of 92% after removing the solvent from the crude product by evaporation.

Next, 600 g of water was mixed with 188 g (0.7 mol) of (1-hydroxycyclohexyl) benzyl bromide. The mixture was stirred at 100° C. for 1 hour and then cooled to room temperature. 76 g (1.11 mol) of 50% hydrogen peroxide was slowly added into the mixture under ice bath, and then the mixture was irradiated by a visible light lamp (with a wavelength of about 400 nm) for 6 hours to form a crude product (in an organic layer). After extracted with DCE and brine and evaporated to remove the solvent, (1-hydroxycy-clohexyl)-phenyl-methanone was produced with a yield of 65%. (bp. 175° C./15 mmHg)

Example 4

Synthesis of 2-methyl-1-phenylpropan-1-one

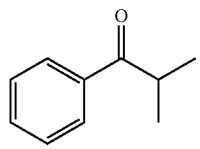

53 g (0.78 mol) of 50%0 hydrogen peroxide was slowly added into a mixture of 100 g (0.745 mol) of isobutylbenzene and 251 g (1.49 mol) of hydrobromic acid in 1000 g of DCE under ice bath. The resulting mixture was irradiated by a visible light lamp (with a wavelength of about 400 nm) for 8 hours. After allowing the mixture to stand for a sufficient time to produce an organic layer and an aqueous layer separated from each other, (1-bromo-2-methylpropyl)-benzene was produced with a yield of 95% by removing the solvent from the organic layer via evaporation.

Next, 600 g of water was mixed with 149 g (0.7 mol) of (1-bromo-2-methylpropyl)benzene prepared as stated above. The mixture was stirred at 100° C. for 1 hour then cooled to room temperature. 76 g (1.11 mol) of 50% hydrogen peroxide was slowly added into the mixture under ice bath, and then the mixture was irradiated by a visible light lamp (with a wavelength of about 400 nm) for 6 hours to form a crude product (in an organic layer). After extracted with DCE and brine and evaporated to remove the solvent, 2-methyl-1-phenylpropan-1-one was produced with a yield of 80%. (bp. 217° C.)

Example 5

One-Pot Method for Synthesizing
2-methyl-1-phenylpropan-1-one

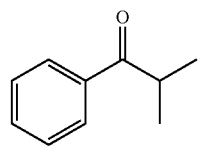

To 100 g (0.745 mol) of isobutylbenzene and 63 g (0.373 mol) of hydrobromic acid in 1000 g of DCE was slowly added 127 g (1.86 mol) of 50% hydrogen peroxide at 60° C. and the mixture was irradiated by a visible light lamp (with a wavelength of about 400 nm) for 12 hours to form a crude product (in an organic layer). After extracted with DCE and brine and evaporated to remove the solvent, 2-methyl-1-phenylpropan-1-one was obtained with a yield of 70%. (bp. 217° C.)

Example 6

One-Pot Method for Synthesizing
α-oxo-benzeneacetic acid methyl ester

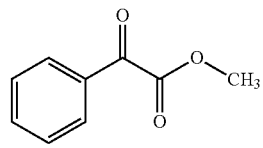

To 100 g (0.667 mol) of methyl 2-phenylacetate and 33.7 g (0.2 mol) of hydrobromic acid was slowly added 68 g (1 mol) of 50% hydrogen peroxide at 60° C. The mixture was irradiated by a visible light lamp (with a wavelength of about 400 nm) for 12 hours to form a crude product (in an organic layer). After extracted with DCE and brine and evaporated to remove the solvent, α-oxo-benzeneacetic acid methyl ester was obtained with a yield of 75%. (bp. 246-248° C.)

Example 7

Synthesis of 2-hydroxy-1-[4-[4-(2-hydroxy-2-methylpropyl)phenyl]phenyl]-2-methylpropan-1-one

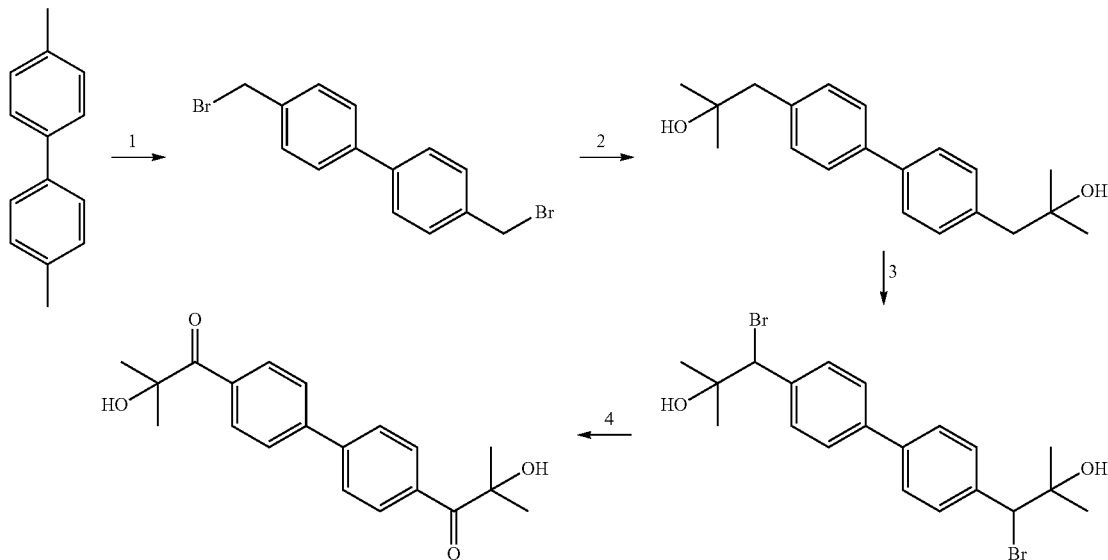

Step 1: 82 g (1.2 mol) of 50% hydrogen peroxide was slowly added into a mixture of 100 g (0.55 mol) of 4,4'-dimethyl-1,1'-biphenyl and 370 g (2.2 mol) of hydrobromic acid in 1000 g of DCE under ice bath. The resulting mixture was irradiated by a visible light lamp (with a wavelength of about 400 nm) for 12 hours to form a crude product (in an organic layer). 4,4'-bis(bromomethyl)-1,1'-biphenyl was obtained with a yield of 75% after removing the solvent from the crude product by evaporation.

Step 2: 340 g (1 mol) of 4,4'-bis(bromomethyl)-1,1'-biphenyl was slowly added into 73 g (3 mol) of magnesium powder in 1000 g of dry THF to form a first mixture. The first mixture was gently heated to 50'C and stirred for 1 hour, and then 139 g (2.4 mol) of anhydrous acetone was slowly added to form a second mixture. The second mixture was heated to reflux for 8 hours. After cooling to room temperature, 1000 g of 10% hydrochloric acid was added to the second mixture, followed by extraction with 500 g of dichloromethane twice. Upon separation of the phases, the organic layer was dried with a desiccant (magnesium sulfate). A yellow solid product, 1,1'-([1,1'-biphenyl]-4,4'-diyl)bis(2-methylpropan-2-ol), was obtained with a yield of 80% after the removal of desiccant and solvent from the organic layer.

Step 3: To 222 g (0.745 mol) of 1,1'-([1,1'-biphenyl]-4,4'-diyl)bis(2-methylpropan-2-ol) and 56 g (0.82 mol) of 50% hydrogen peroxide in 1000 g of DCE was slowly added 252 g (1.5 mol) of hydrobromic acid under ice bath. The mixture was irradiated by a visible light lamp (with a wavelength of about 400 nm) for 8 hours to form a crude product (in an organic layer). 1,1'-([1,1'-biphenyl]-4,4'-diyl)bis(1-bromo-2-methylpropan-2-ol) was obtained with a yield of 90% after removing the solvent from the crude product by evaporation.

Step 4: 1280 g of water was mixed with 319 g (0.7 mol) of 1,1'-([1,1'-biphenyl]-4,4'-diyl)bis(1-bromo-2-methylpropan-2-ol), stirred at 100° C. for 1 hour and then cooled to room temperature. 76 g (1.11 mol) of 50% hydrogen peroxide was slowly added into the mixture under ice bath, and the mixture was irradiated by a visible light lamp (with a wavelength of about 400 nm) for 6 hours to form a crude product (in an organic layer). 2-hydroxy-1-[4-[4-(2-hydroxy-2-methylpropanoyl)phenyl]phenyl]-2-methylpropan-1-one was obtained with a yield of 70% after removing the solvent from the crude product by evaporation. (bp. 517° C.)

Example 8

Synthesis of 1,1'-(oxybis(4,1-phenylene))bis(2-hydroxy-2-methylpropan-1-one)

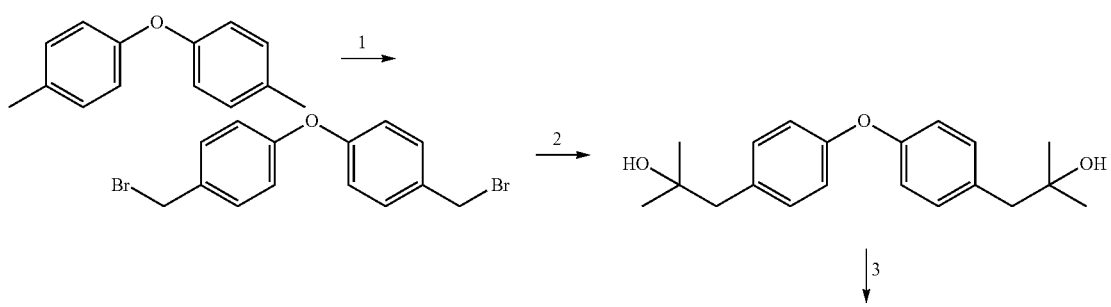

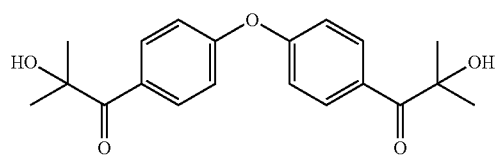
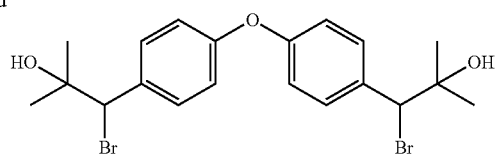

Step 1: 82 g (1.2 mol) of 50% hydrogen peroxide was slowly added into a mixture of 109 g (0.55 mol) of 4,4'-oxybis(methylbenzene) and 370 g (2.2 mol) of hydrobromic acid in 1000 g of DCE under ice bath. The resulting mixture was irradiated by a visible light lamp (with a wavelength of about 400 nm) for 12 hours to form a crude product (in an organic layer). 4,4'-oxybis((bromomethyl)benzene) was obtained with a yield of 650% after removing the solvent from the crude product by evaporation.

Step 2: 356 g (1 mol) of 4,4'-oxybis((bromomethyl)benzene) was slowly added into 73 g (3 mol) of magnesium powder and 1000 g of dry THF to form a first mixture. The first mixture was gently heated to 50° C. and stirred for 1 hour, and then 139 g (2.4 mol) of anhydrous acetone was slowly added to form a second mixture. The second mixture was heated to reflux for 8 hours. After cooling to room temperature, 1000 g of 10% hydrochloric acid was added to the second mixture, followed by extraction with 500 g of dichloromethane twice. Upon separation of the phases, the organic layer was dried with a desiccant (magnesium sulfate). A yellow solid product, 1,1'-(oxybis(4,1-phenylene))bis(2-methylpropan-2-ol), was obtained with a yield of 85% after the removal of desiccant and solvent from the organic layer.

Step 3: To 234 g (0.745 mol) of 1,1'-(oxybis(4,1-phenylene))bis(2-methylpropan-2-ol) and 56 g (0.82 mol) of 50° % hydrogen peroxide in 1000 g of DCE was slowly added 252 g (1.5 mol) of hydrobromic acid under ice bath. The mixture was irradiated by a visible light lamp (with a wavelength of about 400 nm) for 8 hours to form a crude product (in an organic layer). 1,1'-(oxybis(4,1-phenylene))bis(1-bromo-2-methylpropan-2-ol) was obtained with a yield of 90% after removing the solvent from the crude product by evaporation.

Step 4: 1320 g of water was mixed with 330 g (0.7 mol) of 1,1'-(oxybis(4,1-phenylene))bis(1-bromo-2-methylpropan-2-ol), stirred at 100'C for 1 hour and then cooled to room temperature. 76 g (1.11 mol) of 50% hydrogen peroxide was slowly added into the mixture under ice bath, and the mixture was irradiated by a visible light lamp (with a wavelength of about 400 nm) for 6 hours to form a crude product (in an organic layer). 1,1'-(oxybis(4,1-phenylene))bis(2-hydroxy-2-methylpropan-1-one) was obtained with a yield of 75% after removing the solvent from the crude product by evaporation. (bp. 502-504° C.)

Example 9

Synthesis of 1,1'-propane-2,2-diylbis(4,1-phenylene))bis(2-hydroxy-2-methylpropan-1-one)

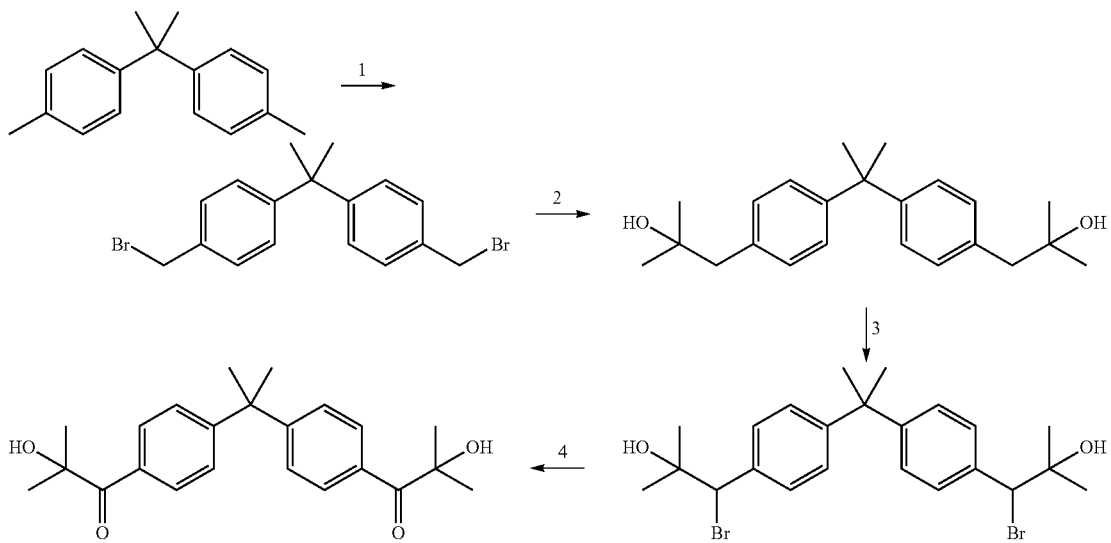

Step 1: 82 g (1.2 mol) of 50% hydrogen peroxide was slowly added into a mixture of 123 g (0.55 mol) of 4,4'-(propane-2,2-diyl)bis(methylbenzene) and 370 g (2.2 mol) of hydrobromic acid in 1000 g of DCE under ice bath. The resulting mixture was irradiated by a visible light lamp (with a wavelength of about 400 nm) for 12 hours to form a crude product (in an organic layer). 4,4'-(propane-2,2-diyl)bis((bromomethyl)benzene) was obtained with a yield of 85% after removing the solvent from the crude product by evaporation.

Step 2: 382 g (1 mol) of 4,4'-(propane-2,2-diyl)bis((bromomethyl)benzene) was slowly added into 73 g (3 mol) of magnesium powder and 1000 g of dry THF to form a first mixture. The first mixture was gently heated to 50° C. and stirred for 1 hour, and then 139 g (2.4 mol) of anhydrous acetone was slowly added to form a second mixture. The second mixture was heated to reflux for 8 hours. After cooling to room temperature, 1000 g of 10% hydrochloric acid was added, followed by extraction with 500 g of dichloromethane twice. Upon separation of the phases, the organic layer was dried with a desiccant (magnesium sulfate). A yellow solid product, 1,1'-(propane-2,2-diylbis(4,1-phenylene))bis(2-methylpropan-2-ol), was obtained with a yield of 85% after the removal of desiccant and solvent from the organic layer.

Step 3: To 253 g (0.745 mol) of 1,1'-(propane-2,2-diylbis (4,1-phenylene))bis(2-methylpropan-2-ol) and 56 g (0.82 mol) of 50% hydrogen peroxide in 1000 g of DCE was slowly added 252 g (1.5 mol) of hydrobromic acid under ice bath. The mixture was irradiated by a visible light lamp (with a wavelength of about 400 nm) for 8 hours to form a crude product (in an organic layer). 1,1'-(propane-2,2-diyl-bis(4,1-phenylene))bis(1-bromo-2-methylpropan-2-ol) was obtained with a yield of 90% after removing the solvent from the crude product by evaporation.

Step 4: 1396 g of water was mixed with 349 g (0.7 mol) of 1,1'-(propane-2,2-diylbis(4,1-phenylene))bis(1-bromo-2-methylpropan-2-ol), stirred at 100 degree for 1 hour and then cooled to room temperature. 76 g (1.11 mol) of 50% hydrogen peroxide was slowly added into the mixture under ice bath, and the mixture was irradiated by a visible light lamp (with a wavelength of about 400 nm) for 6 hours to form a crude product (in an organic layer). 1,1'-(propane-2, 2-diylbis(4,1-phenylene))bis(2-hydroxy-2-methylpropan-1-one), was obtained with a yield of 85% after removing the solvent from the crude product by evaporation. (bp. 574° C.)

Example 10

Synthesis of 2-methyl-phenylpropan-1-one

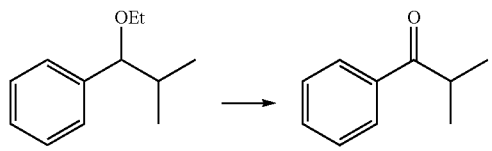

17.8 g (0.1 mol) of (1-ethoxy-2-methyl-propyl)benzene was mixed with 17 g (0.1 mol) of hydrobromic acid and 20 g of cyclohexane under ice bath, and 7 g (0.1 mol) of 50% hydrogen peroxide was slowly added into the mixture and then the mixture was irradiated by a visible light lamp (with a wavelength of about 400 nm) for 3 hours. The organic layer was separated from the mixture and further extracted with 10 g water. The extracted organic layer was collected and concentrated to dryness to give 12 g of 2-methyl-1-phenylpropan-1-one (yield 80%). (bp. 217° C.)

Example 11

Synthesis of phenyl-[4-(phenylcarbonyl))cyclohexyl]methanone

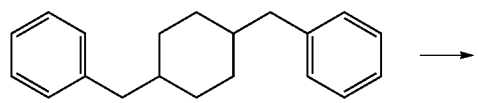

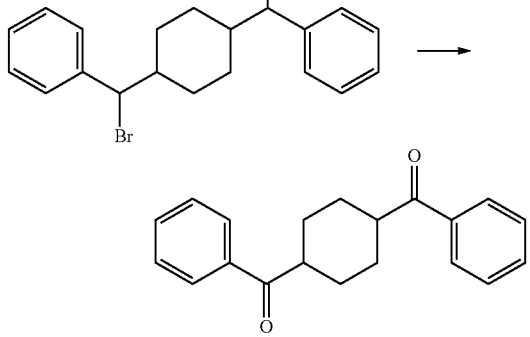

Step 1: 143 g (2.1 mol) of 50% hydrogen peroxide was slowly added into a first mixture of 264 g (1 mol) of 1,4-Dibenzylcyclohexane (from 3B Scientific Corporation), 674 g (4 mol) of hydrobromic acid and 500 g of cyclohexane under ice bath to form a second mixture, and the second mixture was irradiated by a visible light lamp (with a wavelength of about 400 nm) for 8 hours. The organic layer was separated from the aqueous layer and further extracted with 100 g water. The extracted organic layer was collected and concentrated to dryness to give 316 g of 1,4-bis(α-bromobenzyl)-cyclohexane (yield: 75%).

Step 2: 316 g (0.75 mol) of 1,4-bis(α-bromobenzyl)-cyclohexane obtained from Step 1 and 2532 g of water were mixed and heated to reflux for 8 hours to form a third mixture. After cooling to room temperature, water was removed by filtration. The remaining solid was mixed with 250 g of cyclohexane and 126 g (0.75 mol) of hydrobromic acid under ice bath to form a fourth mixture. 106 g (1.55 mol) of 50% hydrogen peroxide was slowly added into the fourth mixture to form a fifth mixture, and the fifth mixture was irradiated by a visible light lamp (with a wavelength of about 400 nm) for 8 hours. The organic layer was separated from the aqueous layer and further extracted with 100 g water. The extracted organic layer was collected and concentrated to dryness to give 175 g of phenyl-[4-(phenyl carbonyl)cyclohexyl]methanone (yield: 80%, bp. 437° C.).

The above disclosure is related to the detailed technical contents and inventive features thereof. Persons of ordinary skill in the art may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

We claim:

1. A process for preparing a compound of formula (I), (II), (III) or (IV):

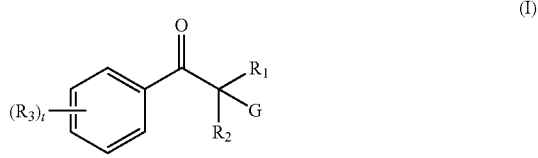

-continued

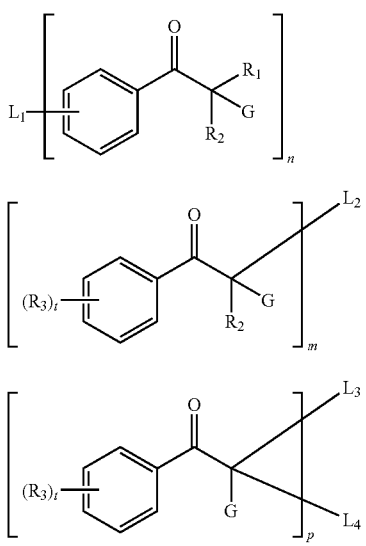

said process comprising photo-oxidizing a corresponding compound of formula (V), (VI), (VII) or (VIII):

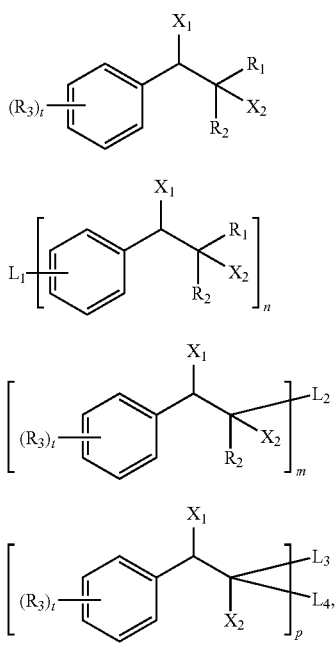

in the presence of an oxidative system comprising at least one bromide compound, wherein:

$X_1$ represents —H, halo, —OH or —$OR_4$;
$X_2$ represents —H, —OH, nitro, —$N(R_4)_2$, —$NHR_4$, —$R_4$, —$OR_4$, —$NR_4OH$, —$ONHR_4$, $Si(R_4)_3$, —$OSi(R_4)_3$, —$P(R_4)_2$, —$P(=O)(OR_4)_2$, —$P(=O)(R_4)_2$, or a 5- or 6-membered nitrogen-linked heterocyclyl having one or two heteroatoms selected from N, O or S in which at least one heteroatom is N, with the proviso that when $X_1$ represents —OH, $X_2$ is not —OH or —$OR_4$;
$R_1$ and $R_2$ independently represent alkyl, cycloalkyl, heterocycloalkyl, aryl, heteroaryl, amino, amido, or an organic moiety comprising at least one of phosphor, oxygen, nitrogen and silicon, or $R_1$ and $R_2$, together with the carbon atom to which they attach, form a "—C=O" radical or a ring structure;
$R_3$ represents H, alkyl, cycloalkyl, aryl, heteroaryl, amino or amido;
t represents an integer from 1 to 5;
G represents —H, halo, —OH, nitro, —$N(R_4)_2$, —$NHR_4$, —$R_4$, —$OR_4$, —$NR_4OH$, —$ONHR_4$, —$Si(R_4)_3$, —$OSi(R_4)_3$, —$P(R_4)_2$, —$P(=O)(OR_4)_2$, —$P(=O)(R_4)_2$, or a 5- or 6-membered nitrogen-linked heterocyclyl having one or two heteroatoms selected from N, O or S in which at least one heteroatom is N;
$R_4$ represents alkyl or aryl;
n, m and p independently represent an integer from 2 to 6;
$L_1$ represents an n-valent linking group;
$L_2$ represents an m-valent linking group; and
$L_3$ and $L_4$ represent a p-valent linking group and can be the same or different from each other.

2. The process according to claim 1, wherein the compound of formula (II) has formula (II'), (II") or (II'''):

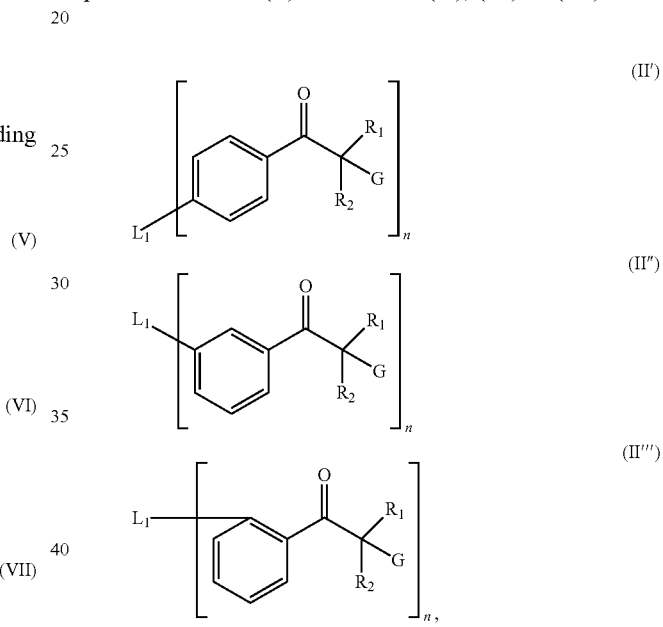

$R_1$, $R_2$, G, $L_1$ and n have the meanings given in claim 1.

3. The process according to claim 1, wherein $X_1$ is H and $X_2$ is —OH or —$OR_4$.

4. The process according to claim 3, wherein the compound of formula (V), (VI), (VII) or (VIII) is obtained by an organic metal reaction.

5. The process according to claim 4, wherein the organic metal reaction is conducted by reacting a compound of formula (IX):

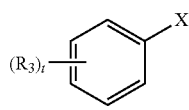

with a compound of formula (X):

$$R_1C(=O)R_2 \qquad (X)$$

in the presence of magnesium, zinc or tin to form the compound of formula (V), wherein $R_1$, $R_2$, $R_3$, and t are as defined in claim 1 and X is halo.

6. The process according to claim 1, wherein $X_1$ is —OH.

7. The process according to claim 1, wherein $X_1$ is H and $X_2$ is not —OH or —$OR_4$.

8. The process according to claim 1, wherein $R_1$ and $R_2$ independently represent $C_{1-3}$ alkyl or $R_1$ and $R_2$, together with the carbon atom to which they attach, form $C_{3-8}$cycloalkyl; and G is —Br or —OH.

9. The process according to claim 1, wherein $R_3$ is hydrogen.

10. The process according to claim 1, wherein the oxidative system further comprises one or more peroxides selected from hydrogen peroxide ($H_2O_2$), sodium peroxide ($Na_2O_2$), potassium peroxide ($K_2O_2$), calcium peroxide ($CaO_2$), magnesium peroxide ($MgO_2$), zinc peroxide ($ZnO_2$), strontium peroxide ($SrO_2$), organic peroxide and a combination thereof.

11. The process according to claim 1, wherein the bromide compound is selected from $Br_2$, HBr, HOBr or $M(Br)_k$, wherein M is a metal ion selected from alkali metals or alkaline earth metals and k equals to the valency of M.

12. The process according to claim 1, wherein the oxidative system is selected from $Br_2$, $Br_2/H_2O_2$, $HBr/H_2O_2$, $HBr/Cl_2$, bromide/acid/$H_2O_2$, bromide/chlorine gas, HBr/halogen acid, HBr/hypohalite, bromide/acid/halide salts, bromide salts/acid/$H_2O_2$ and bromide/acid/hypohalite and wherein the acid is selected from sulfuric acid, hydrochloric acid, hydrobromic acid, nitric acid, phosphoric acid, acetic acid, hydroiodic acid and any combination thereof.

13. The process according to claim 1, wherein both of $X_1$ and $X_2$ in the compound of formula (V), (VI), (VII) or (VIII) represent H, and G in the compound of formula (I), (II), (III) or (IV) represents —H.

14. The process according to claim 13, wherein the compound of formula (I), (II), (III) or (IV) where G represents —H is further reacted with a chloride, bromide or iodine compound and hydrolyzed to form the compound of formula (I), (II), (III) or (IV) where G represents —OH.

15. The process according to claim 1, wherein G is halo and each of the compound of formulae (I), (II), (III) or (IV) is respectively converted to a compound of formula (I-1), (II-1), (III-1) or (IV-1) in the presence of a base:

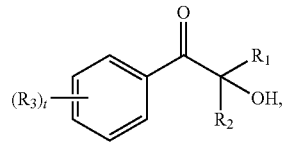
(I-1)

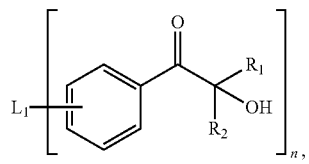
(II-1)

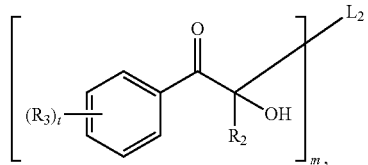
(III-1)

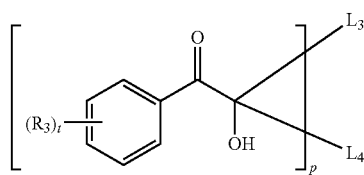
(IV-1)

wherein $R_1$, $R_2$, $R_3$, $L_1$, $L_2$, $L_3$ and $L_4$, t, n, m, p are as described in claim 1.

16. The process according to claim 1, wherein the linking group of $L_1$, $L_2$, $L_3$ and $L_4$ are each independently a direct bond, amine, amido, a di-, tri- tetra- penta- or hexa-valent aliphatic or aromatic group or a di-, tri- tetra- penta- or hexa-valent organic group containing at least one S, P, O, N or Si atom.

17. The process according to claim 1, which is a one-pot process.

18. The process according to claim 1, wherein $X_1$ is —$OR_4$.

19. The process according to claim 1, wherein $X_1$ is halo.